United States Patent
Veile

(10) Patent No.: US 9,796,489 B2
(45) Date of Patent: Oct. 24, 2017

(54) METHOD AND DEVICE FOR FILLING AND CLOSING PHARMACEUTICAL OBJECTS

(75) Inventor: Josef Veile, Westhausen (DE)

(73) Assignee: Groninger & Co. GmbH, Crailsheim (DE)

( * ) Notice: Subject to any disclaimer, the term of this patent is extended or adjusted under 35 U.S.C. 154(b) by 704 days.

(21) Appl. No.: 13/596,192

(22) Filed: Aug. 28, 2012

(65) Prior Publication Data

US 2013/0067867 A1    Mar. 21, 2013

(30) Foreign Application Priority Data

Sep. 15, 2011    (DE) .................. 10 2011 113 358

(51) Int. Cl.
| | |
|---|---|
| B65B 43/42 | (2006.01) |
| B65B 57/00 | (2006.01) |
| B65B 3/00 | (2006.01) |
| B65B 61/28 | (2006.01) |

(52) U.S. Cl.
CPC ............. *B65B 3/003* (2013.01); *B65B 43/42* (2013.01); *B65B 61/28* (2013.01); *A61M 2207/00* (2013.01); *A61M 2209/045* (2013.01)

(58) Field of Classification Search
CPC .. B65B 3/00; B65B 3/003; B65B 3/26; B65B 3/28; B65B 39/006; B65B 1/46; B65B 43/42–43/60; B65B 5/08; B65B 65/00; B65B 65/003; B65B 65/006; B65B 3/006; G01G 15/00; G01N 2035/041; G01N 2035/046; G01N 2035/0465; G01N 35/04
USPC ...................... 53/467–471, 284.5, 249–252; 414/416.03; 141/83
See application file for complete search history.

(56) References Cited

U.S. PATENT DOCUMENTS

| | | | | |
|---|---|---|---|---|
| 2,967,633 | A * | 1/1961 | Stegemann ............... | G01N 1/18 414/416.03 |
| 3,939,626 | A * | 2/1976 | Cioni et al. ..................... | 53/167 |
| 3,940,909 | A * | 3/1976 | Cioni et al. ..................... | 53/167 |
| 4,982,553 | A * | 1/1991 | Itoh .......................... | B67B 7/02 198/346.2 |
| 5,156,193 | A * | 10/1992 | Baruffato et al. ................ | 141/1 |

(Continued)

FOREIGN PATENT DOCUMENTS

| | | |
|---|---|---|
| DE | 100 28 823 | 12/2001 |
| DE | 10028823 A1 * | 5/2002 |

(Continued)

OTHER PUBLICATIONS

"Annotated Translation of DE10028823", machine translated on Jun. 9, 2016, 10 pages.*

*Primary Examiner* — Stephen F Gerrity
*Assistant Examiner* — Joshua Kotis
(74) *Attorney, Agent, or Firm* — Michael J. Striker

(57) ABSTRACT

A method for filling and closing pharmaceutical objects disposed in parallel rows in nests includes removing the objects from the nests at an inlet of a conveying device in a removal station and placing the objects into the conveying device. In the conveying device, the objects are fed in succession to a first weighing station and weighed, to filling station and filled and to a second weighing station and again weighed and to a closing station and/or crimping station and closed. After closing, the objects are removed from the conveying section. In every case, pre-sterilized objects are processed in an aseptic manner.

15 Claims, 2 Drawing Sheets

(56) References Cited

U.S. PATENT DOCUMENTS

| | | | | |
|---|---|---|---|---|
| 5,158,895 A * | 10/1992 | Ashihara | G01N 33/53 | |
| | | | 422/65 | |
| 5,673,535 A * | 10/1997 | Jagger | B65B 55/027 | |
| | | | 198/803.14 | |
| 5,806,287 A * | 9/1998 | Trechsel | 53/502 | |
| 6,151,535 A * | 11/2000 | Ehlers | G01N 35/04 | |
| | | | 198/340 | |
| 6,293,387 B1 * | 9/2001 | Forster | 198/377.02 | |
| 6,800,818 B2 * | 10/2004 | Balboni et al. | 177/52 | |
| 7,421,833 B2 * | 9/2008 | Rothbauer et al. | 53/471 | |
| 7,503,353 B2 * | 3/2009 | Monte | 141/1 | |
| 7,549,275 B2 * | 6/2009 | Monti | 53/502 | |
| 8,453,686 B2 * | 6/2013 | Klaus | B65B 3/16 | |
| | | | 141/139 | |
| 8,601,777 B2 * | 12/2013 | Monti | 53/502 | |
| 2005/0042710 A1 * | 2/2005 | Oshima et al. | 435/31 | |
| 2005/0060962 A1 * | 3/2005 | Rothbauer | B65B 3/28 | |
| | | | 53/471 | |
| 2008/0273946 A1 * | 11/2008 | Monti | 414/21 | |
| 2009/0003981 A1 * | 1/2009 | Miller | B65G 1/04 | |
| | | | 414/267 | |
| 2009/0094940 A1 * | 4/2009 | Py | A23L 2/46 | |
| | | | 53/267 | |
| 2010/0150780 A1 * | 6/2010 | Hamada | G01N 15/04 | |
| | | | 422/65 | |
| 2011/0094189 A1 * | 4/2011 | Bottger et al. | 53/425 | |
| 2011/0158850 A1 * | 6/2011 | Pedrazzini | B01L 9/02 | |
| | | | 422/65 | |
| 2012/0090268 A1 * | 4/2012 | Krauss et al. | 53/281 | |
| 2012/0210675 A1 * | 8/2012 | Murray et al. | 53/403 | |

FOREIGN PATENT DOCUMENTS

| | | |
|---|---|---|
| DE | 10 2005 006 733 | 8/2006 |
| DE | 102005006733 A1 * | 8/2006 |
| DE | 102009027452 | 1/2011 |
| DE | 102009027452 A1 * | 5/2011 |
| WO | 2009/153018 | 12/2009 |

* cited by examiner

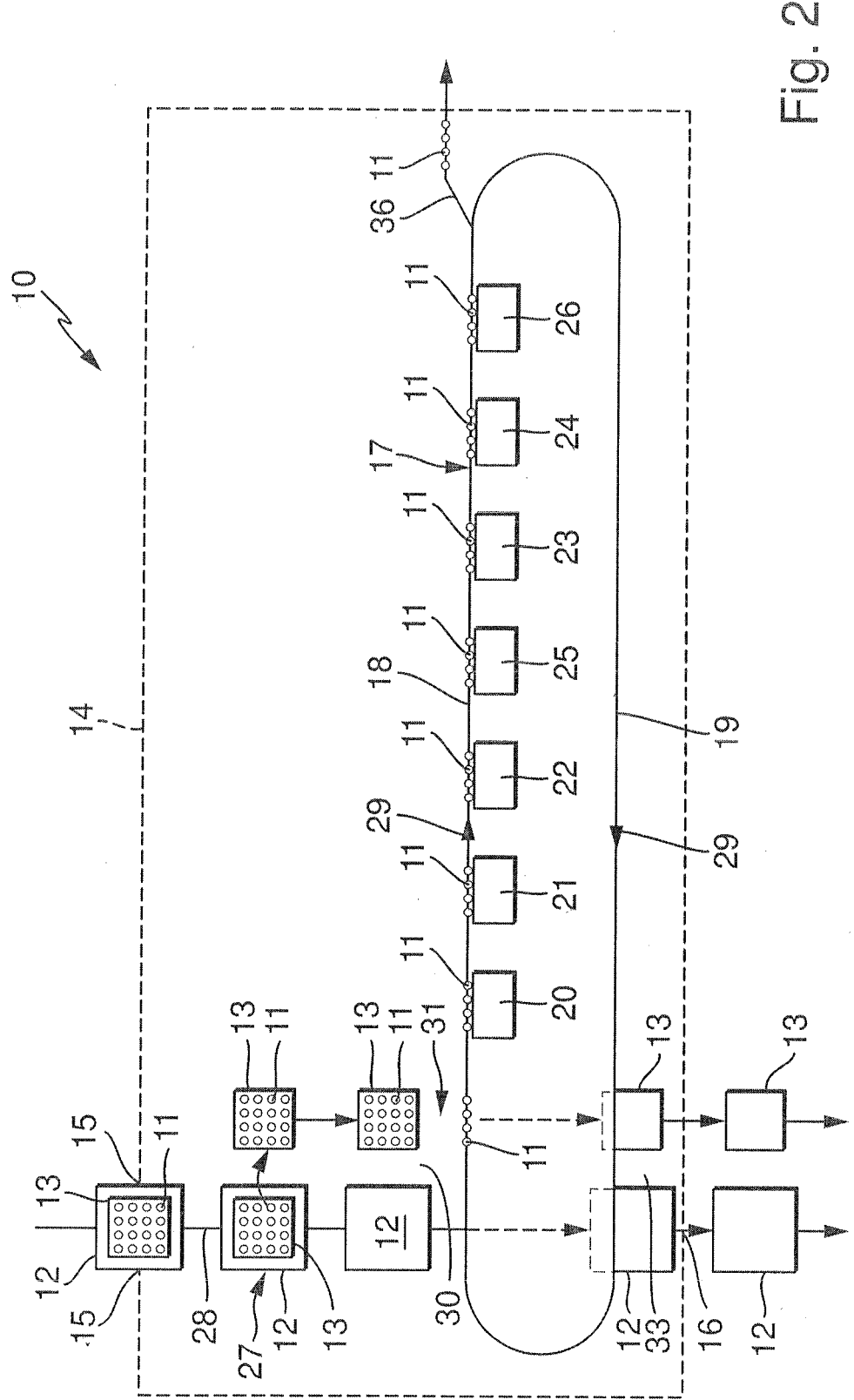

METHOD AND DEVICE FOR FILLING AND CLOSING PHARMACEUTICAL OBJECTS

CROSS-REFERENCE TO A RELATED APPLICATION

The invention described and claimed hereinbelow is also described in German Patent Application DE 10 2011 113 358.9 filed on Sep. 15, 2011. This German Patent Application, subject matter of which is incorporated herein by reference, provides the basis for a claim of priority of invention under 35 U.S.C. 119(a)-(d).

BACKGROUND OF THE INVENTION

The invention relates to a novel method and a device for filling and closing pharmaceutical objects, e.g. syringes, vials, cylindrical ampules or the like, which are disposed in parallel rows in nests.

Methods for filling and closing pharmaceutical objects are known in which the processing/treatment of the objects takes place primarily in the state in which the objects are located in nests. Nests as known in the art are substantially plate-shaped receiving devices that contain recesses in which the objects are accommodated in a form-fit manner. In the conventional methods, in which the objects remain in the nests during processing, is advantageous per se because the objects are present in the nests in a sorted and oriented manner and can be processed directly in this manner. In the processing stations, in which the objects are processed individually, e.g. weighing stations, each object is lifted out of the nest, even several times if necessary, and returned to the nest.

In one known method, the objects are first lifted out of the nest and than pass through processing stations such as a weighing station, a filling station and a weighing station and are then returned to the nest. In another known method, the objects are lifted out of the nest, are weighed in the weighing station, are returned to the nest, are filled in the filling station, are lifted out of the nest once more and weighed and are then returned to the nest. In the closing station, where stoppers are inserted, the objects are located in the nest. It is disadvantageous, however, that the objects are required to be repeatedly lifted out of the nests and replaced therein. Repeatedly lifting and returning objects to the nest results in correspondingly long processing times. The plurality of handling motions of the objects can result in damage to the product, for example, the objects can inadvertently touch one another.

SUMMARY OF THE INVENTION

The present invention overcomes the shortcomings of known arts, such as those mentioned above.

The invention provides a method and a device for filling and closing pharmaceutical objects, which make it possible to increase the output of filling and closing at very high precision and with 100% inspection of the fill quantity. The method and device further operate to rule out or minimize possible damage to the product by reducing handling motions.

In a method for filling and closing pharmaceutical objects, e.g. syringes, vials, cylindrical ampules or the like, the invention implements the following method steps: The objects are removed from the nests at an inlet of a conveying device in a removal station and are placed into the conveying device; by way of the conveying device, the objects are fed along a straight section of the conveying section in succession to a first weighing station, in which the objects are weighed, to a filling station, in which the objects are filled, and to a second weighing station, in which the filled objects are weighed once more. The filled objects are then fed to a closing station and/or a crimping station, in which the filled objects are closed. The filled objects can then be removed from the conveying section. The objects to be processed are pre-sterilized. Processing takes place aseptically.

Alternatively, the invention provides a device for filling and closing pharmaceutical objects, e.g. syringes, vials, cylindrical ampules or the like, wherein the objects are disposed in parallel rows in nests, which are removably inserted into an approximately tub-shaped, box-like transport container (tub). The device comprises a conveying device, along the conveying sections of which individual processing stations for the objects are disposed, for example, for weighing, filling and closing the objects. A lifting station for removing the nest from the tub is provided at the inlet of the conveying device. The lifting station is followed by a removal station for removing an object row from the nest and transferring it to the conveying device. The objects removed from the nest are fed by way of the conveying device to the individual processing stations, where they are processed using all the processing steps and, at the end, in an insertion station, are either placed into the nest that has already been inserted into the tub in an insertion station or are subsequently inserted into the tub. Alternatively, the objects are removed individually from the conveying device.

The method and the device according to the invention therefore provide that, at the beginning, the objects are lifted out of the nest once and are than processed completely using all the processing steps. After completing all of the processing steps, i.e., at the end, the objects are either separated and removed from the conveying device without having been replaced in the nest or, instead, are returned to the nest, which has either been previously placed into the tub or is subsequently placed therein, wherein the tub then leaves the device.

The method according to the invention has that many more advantages the more processing stations the device comprises. Advantageously, the objects are conveyed in a contactless manner during conveyance by way of the conveying device along the processing stations. It is possible to perform a 100% inspection of the fill quantity during filling in the filling station without greater drops in output. In the case of objects in the form of vials, in addition to closing in the closing station by inserting a stopper, it is also possible for crimp caps to be crimped. Since the objects need be handled only once when removed from the nests and once when replaced into the nests (after all the processing steps have been completed), fewer handling motions take place and therefore the risk of the product becoming damaged is eliminated or at least largely minimized. With respect to the individual processing of the objects described, it is furthermore advantageous that there is an unobstructed view of the particular object. Optical test methods are made possible as a result, therefore, e.g. measuring the insertion depth when closure takes place via stopper insertion.

BRIEF DESCRIPTION OF THE DRAWINGS

Further features and advantages of the invention will become apparent from the description of embodiments that follows, with reference to the attached figures, wherein:

FIG. 2 is a schematic depiction, which approximately corresponds to FIG. 1, of a device according to a second exemplary embodiment.

DETAILED DESCRIPTION OF THE PREFERRED EMBODIMENTS

Figure 1:
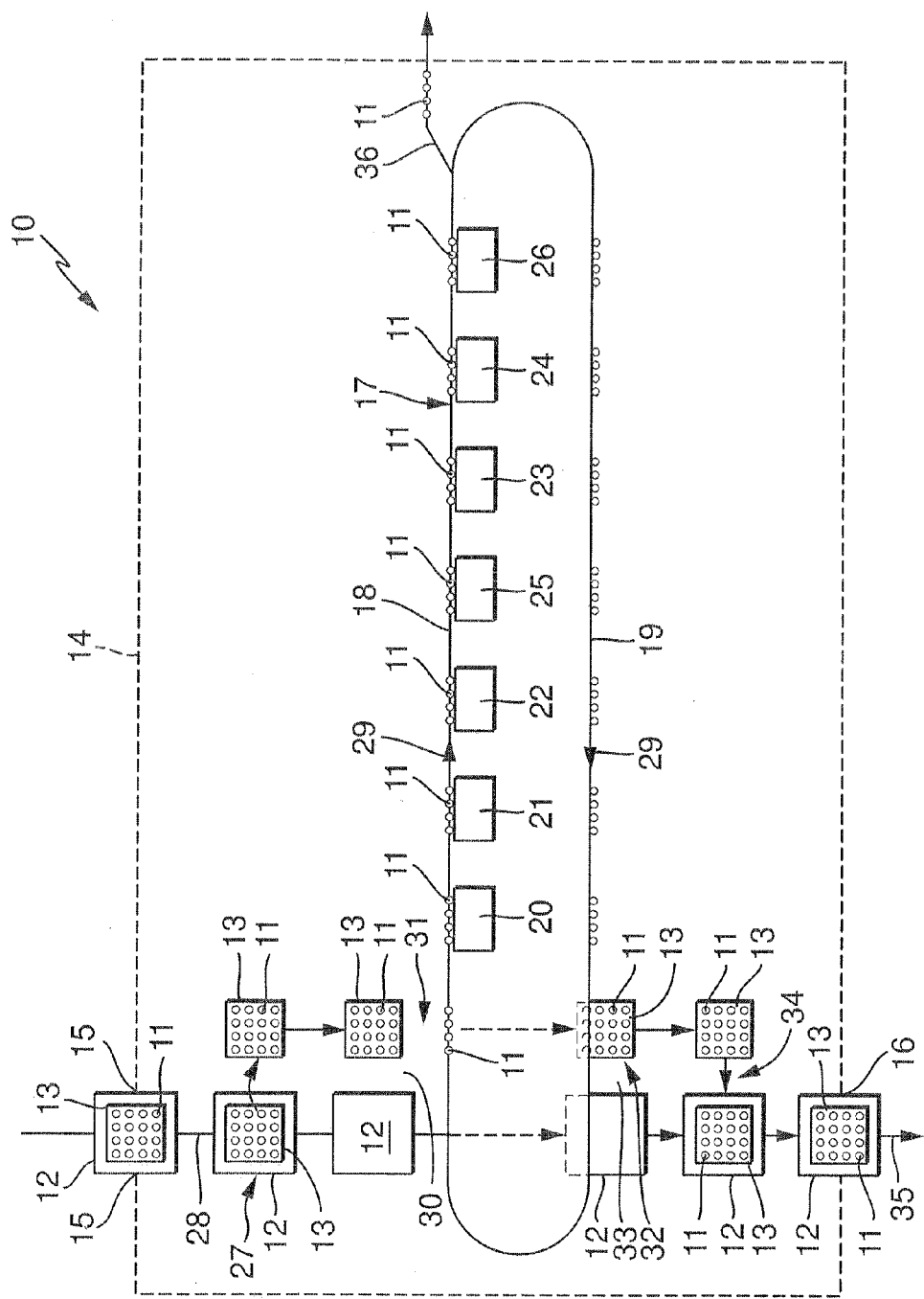
FIG. 1 is a schematic depiction of a device for filling and closing pharmaceutical objects, according to a first exemplary embodiment.

The following is a detailed description of example embodiments of the invention depicted in the accompanying drawings. The example embodiments are presented in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

The device 10 shown in FIG. 1 is designed to process pre-sterilized objects 11 in an aseptic manner, for example, to fill and close pharmaceutical objects 11, which comprise, syringes, vials, cylindrical ampules or like pharmaceutical objects, without limitation.

The objects 11 are fed by way of substantially tub-shaped receiving containers 12 (or "tubs"). The tubs 12 include at least substantially plate-shaped receiving elements, which are equipped with recesses and are typically referred to as a nest 13. The nests are inserted in the tubs 12 and can be removed from the tubs 12 and replaced therein. The objects 11 are disposed in the recesses of the nests 13 in a plurality of rows, next to one another and one behind the other, wherein the rows extend parallel to one another.

The device 10 comprises a housing 14 that is substantially box-like, for example, and is indicated only schematically. In the interior of the housing 14 a laminar flow can be generated, which is oriented, for example, from the cover region of the housing 14 in the approximately vertical direction to the base and is generated via a fan. The housing 14 is equipped with a transfer channel, which is not shown, at both the inlet at 15 and at the outlet at 16. Located in the interior of the housing 14 is a preferably continuously operating conveying device 17. A conveying section of the continuously operating conveying device 17 comprises a straight section 18, which is used as the feed, and a straight section 19, which is used as the return and extends at a lateral distance from the section 18. The two sections 18, 19 are connected at the ends by way of redirection curves.

Along the straight section 18 of the conveying device 17, individual processing stations for the objects 11 are disposed, for example, a weighing station 20, a filling station 21, a second weighing station 22 for weighing filled objects 11, a closing station 23 and a crimping station 24. In the first weighing station 20, the empty, unfilled objects 11 are weighed. In the filling station 21, the objects 11 are filled with pharmaceuticals that can be metered precisely with respect to mass and volume. The filled objects 11 are weighed in the second weighing station 22. The filled objects 11 are closed in the closing station 23. Closing is carried out, for example, via insertion of stoppers, depending on the type of the objects 11. Crimping caps 23 that have been applied can be crimped in the crimping station 24. If desired, a gas-treatment station 25 can be provided downstream of the filling station 11 and upstream and/or downstream of the second weighing station 22. Gas-treatment station 25 is shown following the second weighing station 22. A reject-discarding station 26 is disposed subsequent to the crimping station 24, in which objects 11 that have been identified as rejects are discarded individually.

After passing through the individual processing stations in the region of the section 18, that is, the feed of the conveying device 17, the objects 11 are conveyed back by way of the section 19, that is, the return of the conveying device 17. The individual objects 11 are hung in the form of individual rows in holders of the conveying device 17, which are not depicted further, and remain in this position on the conveying device 17 during processing in the stations.

The distance between the objects 11 can remain the same or changed, for example, widened. The objects 11 are released in the particular weighing station 20 and 22, and therefore only have contact with the weighing plates of the weighing stations 20 or 22. This makes it possible to monitor the fill quantities exactly during weighing in the second weighing station 22. The objects 11 have no contact with one another during conveyance thereof. When the objects 11 are conveyed by way of the conveying device 17 along the individual processing stations, practically no handling motions take place with respect to the objects 11. This feature is advantageous in that it minimizes the possibility that the product will become damaged due to handling motions and action upon the objects 11. The objects 11, which are present in the nests 13 in a sorted and oriented manner, are processed directly in the individual processing stations after removal from the nests 13. An unobstructed view of the objects 11 results, thereby making it possible to use optical test methods, for example, measurement of the insertion depth of a stopper inserted in the closing station 23.

As should be apparent, device 10 makes it possible to remove the objects 11 from the nest 13 at the beginning of the conveying device 17, completely process the objects 11 using all the processing steps and, at the end (as shown in FIG. 1), either insert the objects in the nest 13 or, alternatively (as shown in FIG. 2), remove the objects from the conveying device 17 at the end individually and in a position-specific manner. When the objects 11 are handed off directly (as shown in FIG. 2), without passing through the redirection of the conveying device 17 to the returning section 19 and without being inserted into the nest 13, the objects 11 need not be lifted out of the nest 13 once more for processing steps that typically follow, such as labeling.

The device 10 comprises, at the inlet 30 of the conveying device 17, a schematically shown lifting station 27. In the lifting station 27, nests 13 containing objects 11 are removed from filled tubs 12, which have been fed via a conveyor belt 28 transversely, diagonally or longitudinally, for example, with respect to the conveyance direction 29 of the conveying device 17. The nests 13 are fed to the inlet 30 of the conveying device 17 and a removal station 31 located there. In the removal station 31, the objects 11 are removed from the nest 13 in rows, are transferred to the conveying device 17 and hung there in holders (which are not shown).

The conveying device 17 conveys in a cyclical or continuous manner. Conveyance is partially continuous and partially cyclical also is possible, depending on the type of the particular processing station. The object rows first pass through the first weighing station 20, in which the objects 11, which have been released for weighing, are weighed. The object rows then pass through the filling station 21, in which filling with pharmaceuticals takes place in a metered manner. The object rows are then conveyed to the second weighing station 22, in which the filled objects 11 are weighed once more. Subsequent thereto, the objects 11 can be subjected to gas treatment in the gas-treatment station 25 as needed.

In the subsequent closing station 23, stoppers for closure are inserted, for example, when syringe bodies are the objects 11 or when vials are used. When the objects 11 are vials, or when cylindrical ampules are used, crimping caps are subsequently applied and crimped in the crimping station 24. The device 10 may also comprise test stations, for example cameras, at various points, by way of which a test of the objects 11 in a particular processing stage is carried out. If a test reveals the presence of defects, the objects 11 are removed from the conveying device 17, individually and in a position-specific manner and discarded in the reject-discarding station 26. Objects 11 determined to pass (to be "good") arrive, before or after redirection, for example, by way of the section 19 of the return of the conveying device 17, at an insertion station 32 there. In the insertion station, the filled objects 11 are reinserted into the nests 13.

Immediately after the objects 11 have been lifted out, the nests 13 that have been emptied at the inlet 30 of the removal station 31 are conveyed to the outlet 33 or to another outlet side. For example, the nests are conveyed underneath the conveying device 17, for example, transversely or diagonally or longitudinally, to the conveyance direction according to arrow 29. The nests 13 can then be placed directly in the tubs 12, thereby permitting the processed objects 11 to be placed into the nests 13, which are already contained in the tubs 12.

Alternatively, the nests 13 are initially conveyed to the insertion station 32, where the filled and weighed objects 11 are placed in the nests 13. After the nests 13 are removed in the region of the lifting station 27, the tubs 12 are conveyed towards the output side, for example, underneath the conveying device 17, transversely or diagonally or longitudinally to the conveyance direction according to arrow 29 and, there, to an insertion station 34, in which the nests 13, which are empty or contain filled objects 11, are inserted into the tubs 12. The nests then leave the outlet 16 in the direction transversely or diagonally or longitudinally to the conveyance direction according to arrow 35.

The objects 11, after removal from the nest 13 in the removal station 31, are processed completely in the individual processing stations using all processing steps and, at the end, are returned to the nests 13, which are placed in the tubs 12 immediately after being emptied or after having been filled with objects 11, and finally leave the device 10. The more processing stations that are present in the device 10, the more advantageous the inventive procedure or method, i.e., in which the objects 11 are removed from the nest 13 once at the beginning and are returned to the nests 13 only after having passed through all the processing steps. The objects 11 are spared several instances of contact. Since substantially no handling motions take place by way of action on the objects 11, less damage to the product takes place.

The exemplary embodiment according to FIG. 2 differs from that in FIG. 1 in that the filled objects 11, after passing through the final processing station, for example, the reject-discarding station 26, are handed off in a separated and position-specific manner from the conveying device 17 along a track 36. Track 36 extends longitudinally, diagonally or transversely to the conveying direction according to arrow 29. As shown in FIG. 1, track 36 is provided for carrying away objects that have been identified as faulty in the reject-discarding station 26. The tubs 12, which are empty downstream of the lifting station 27, are conveyed away transversely or diagonally or longitudinally to the conveying device 17 (for example, underneath said conveying device), and are stacked or discarded.

In the same manner, the nests 13, which have become empty after removal of the objects 11 in the region of the removal station 31, also are conveyed away transversely or diagonally or longitudinally to the conveying device 17 (for example, underneath said conveying device), and are stacked or discarded. Objects 11 that are conveyed away via the track 36 can be handed off individually at downstream systems, for inspection, for example. Outflow can take place, for example, upstream or downstream of the redirection and transversely or diagonally or longitudinally to the conveyance direction according to arrow 29.

As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. A method for filling and closing pharmaceutical objects disposed in parallel rows in nests, comprising steps of:
   in a removal station, at an inlet of a conveying device, removing the objects from the nests by first lifting the objects out of the nests once and then placing the objects in the conveying device;
   processing the objects including feeding the objects in succession, one way, along a straight conveying section of the conveying device while carrying out each of the following processing sub-steps:
   first weighing the objects at a first weighing station,
   filling the objects at a filling station,
   second weighing the filled objects at a second weighing station, and
   closing the filled objects at a closing station, a crimping station or both;
   removing the closed filled objects from the straight conveying section of the conveying device, and
   returning the closed filled objects to the nests, at a first insertion station,
   wherein the nests at the inlet of the conveying device are conveyed away from the removal station, to the first insertion station, transversely to the straight conveying section, for use in the step of returning.

2. The method according to claim 1, wherein the straight conveying section redirects the closed filled objects to a straight return section by which the closed filled objects are returned to an outlet provided upstream or downstream of a position of the redirection.

3. The method according to claim 2, wherein the step of processing includes feeding the closed filled objects to the first insertion station, wherein the closed filled objects are placed in the nests.

4. The method according to claim 3, wherein the nests containing the closed filled objects are transferred away from the conveying device.

5. The method according to claim 2, wherein the non-filled objects are removed from the nests in rows and, in the filled state, are placed in nests, which are then dispensed.

6. The method according to claim 1, wherein the nests are contained in tubs, and wherein in the step of removing the objects from the nests, the nests are removed from the tubs in a lifting station at the inlet of the conveying device and, further including, in a second insertion station, returning the nests to the tubs or conveying the nests away upstream of the return.

7. The method according to claim 6, wherein the tubs and/or nests at the inlet of the conveying device are conveyed from the lifting station or from the removal station transversely to the conveying section, to a region of the return section and are conveyed to the second insertion station the insertion station at which the nests provided with filled objects are placed into the tubs or are returned to the first insertion station at which the filled objects are placed in nests.

8. The method according to claim 1, wherein the step of processing includes feeding the filled objects to a gas-treatment station along the conveying section downstream of the filling station and upstream and/or downstream of the second weighing station.

9. The method according to claim 1, wherein the filled objects in the closing station are provided with a stopper.

10. The method according to claim 9, wherein the filled objects in the closing station are crimped in the crimping station.

11. The method according to claim 1, wherein the step of processing includes feeding the filled objects that are identified as rejects to a reject-discarding station where they are discarded individually.

12. The method according to claim 1, wherein the pharmaceutical objects are syringes, vials, cylindrical ampules.

13. The method according to claim 1, wherein processing of the objects is implemented aseptically.

14. The method of claim 1, wherein the objects are placed on the conveying device, processed and returned to the nests in parallel rows.

15. A method for filling and closing pharmaceutical objects disposed in parallel rows in nests, comprising steps of:
   in a removal station, at an inlet of a conveying device, removing the objects from the nests by first lifting the objects out of the nests once and then placing the objects in the conveying device;
   processing the objects including feeding the objects in succession one way along a straight conveying section of the conveying device while carrying out each of the following processing sub-steps:
      first weighing the objects at a first weighing station,
      filling the objects at a filling station,
      second weighing the filled objects at a second weighing station, and
      closing the filled objects at a closing station, a crimping station or both;
   removing the closed filled objects from the straight conveying section of the conveying device,
   carrying a portion of the closed filled objects identified as faulty in a reject-discarding station away from the conveying device, and
   returning another portion of the closed filled objects to the nests at a first insertion station,
   wherein the nests at the inlet of the conveying device are conveyed away from the removal station, to the first insertion station, transversely to the straight conveying section, for use in the step of returning.

* * * * *